United States Patent
Eltorai et al.

(10) Patent No.: US 12,005,151 B2
(45) Date of Patent: Jun. 11, 2024

(54) ANTIMICROBIAL SMARTPHONE FLASHLIGHT

(71) Applicant: Lumen Catheters, LLC, Marlborough, MA (US)

(72) Inventors: Adam E. M. Eltorai, Marlborough, MA (US); Charles W. Henry, Denver, CO (US)

(73) Assignee: Luminary, LLC, Marlborough, MA (US)

(*) Notice: Subject to any disclaimer, the term of this patent is extended or adjusted under 35 U.S.C. 154(b) by 0 days.

(21) Appl. No.: 17/894,500

(22) Filed: Aug. 24, 2022

(65) Prior Publication Data

US 2023/0055664 A1     Feb. 23, 2023

Related U.S. Application Data

(63) Continuation-in-part of application No. 17/464,948, filed on Sep. 2, 2021.

(60) Provisional application No. 63/236,397, filed on Aug. 24, 2021, provisional application No. 63/074,385, filed on Sep. 3, 2020.

(51) Int. Cl.
*A61L 2/24* (2006.01)
*A61L 2/08* (2006.01)
*A61L 2/10* (2006.01)

(52) U.S. Cl.
CPC ............... *A61L 2/24* (2013.01); *A61L 2/084* (2013.01); *A61L 2/10* (2013.01); *A61L 2202/11* (2013.01); *A61L 2202/14* (2013.01); *A61L 2202/16* (2013.01)

(58) Field of Classification Search
CPC .... A61L 2/24; A61L 2/084; A61L 2/10; A61L 2202/11; A61L 2202/14; A61L 2202/16
See application file for complete search history.

(56) References Cited

U.S. PATENT DOCUMENTS

| | | |
|---|---|---|
| 2013/0062534 A1 | 3/2013 | Cole |
| 2013/0323120 A1 | 12/2013 | Ma |
| 2016/0089457 A1 | 3/2016 | Liao et al. |

(Continued)

FOREIGN PATENT DOCUMENTS

| | | | |
|---|---|---|---|
| CN | 103561136 A | | 2/2014 |
| EP | 3575362 A1 | * | 4/2019 |
| KR | 20200073830 A | * | 6/2020 |

OTHER PUBLICATIONS

English machine translation for KR 20200073830A (Year: 2020).*

(Continued)

*Primary Examiner* — Sean E Conley
(74) *Attorney, Agent, or Firm* — Armis IP Law, LLC

(57) ABSTRACT

An integrated light device for invocation from a smartphone includes an antimicrobial light wavelength emanating from a utility light portal of the smartphone. Antimicrobial light, such as those in the so-called UVC range (about 222 nm wavelength) have been shown to effectively decontaminate irradiated surfaces against COVID-19 and other harmful depositions on the surfaces, with minimal harmful radiation to humans. Replacing or controlling a smartphone utility light, such as the LED responsive to a "flashlight" function, allows the personal device to be invoked to quickly irradiate surfaces prior to use, such as sitting, eating, opening doors, and the like.

19 Claims, 3 Drawing Sheets

(56) References Cited

U.S. PATENT DOCUMENTS

2021/0283282 A1  9/2021  Rosen et al.
2021/0346717 A1  11/2021  Young

OTHER PUBLICATIONS

English machine translation for EP 3575362 A1 (Year: 2019).*
International Search Report, PCT/US2022/041332, dated Dec. 8, 2022, pp. 1-4.

* cited by examiner

ANTIMICROBIAL SMARTPHONE FLASHLIGHT

RELATED APPLICATIONS

This patent application claims the benefit under 35 U.S.C. § 119(e) of U.S. Provisional Patent App. No. 63/236,397, filed Aug. 24, 2021, entitled "PERSONAL ANTIMICROBIAL LIGHT DEVICE," and is a Continuation-in-Part (CIP) under 35 U.S.C. § 120 of U.S. patent application Ser. No. 17/464,948, filed Sep. 2, 2021, entitled "ANTIMICROBIAL LIGHT SYSTEMS FOR HIGH-TOUCH SURFACES, APPARATUSES, AND EQUIPMENT," which claims the benefit under 35 U.S.C. § 119(e) of U.S. Provisional Patent App. No. 63/074,385, filed Sep. 3, 2020, entitled "ANTIMICROBIAL LIGHT SYSTEMS FOR HIGH-TOUCH SURFACES, APPARATUSES, AND EQUIPMENT", all incorporated herein by reference in entirety.

BACKGROUND

Surface transmission of pathogens can occur from surfaces touched by multiple people or open to airborne pathogens. Physical contact represents a viable transmission path for many harmful bacterial and viral contaminants. Indirect contact through intermediate surfaces can be mitigated through frequent cleaning of surfaces prone to contact multiple people in a short time, such as handrails, doorknobs, elevator buttons, and the like. Chemical disinfectants are one effective means to keeping commonly touched surfaces free of transmittable disease, however can be labor intensive if done with sufficient regularity. Radiation from certain light sources can also be effective, however the radiation may also be harmful to humans, and thus imposes overhead to contain the radiation.

SUMMARY

An integrated light device for invocation from a smartphone includes an antimicrobial light wavelength emanating from a utility light portal of the smartphone. Antimicrobial light, such as those in the so-called UVC range (about 222 nm wavelength) have been shown to effectively decontaminate irradiated surfaces against COVID-19 and other harmful depositions on the surfaces, with minimal harmful radiation to humans. Replacing or controlling a smartphone utility light, such as the LED (Light-Emitting Diode) responsive to a "flashlight" function, allows the personal device to be invoked to quickly irradiate surfaces prior to use, such as sitting, eating, opening doors, and the like.

Personal electronic devices, often referred to as smartphones or cellphones (or simply "phones"), are as commonplace as car keys, wallets and purses. These personal devices provide a screen and a graphical user interface (GUI) having a utility lighting selection, such that the antimicrobial light wavelength is emitted responsive to the GUI. The utility light is typically provided by an LED integrated into the phone by the phone manufacturer for distribution in new devices. Alternatively, a physical retrofit, upgrade or replacement to the default LED may be performed on the personal device, or certain LEDs may be programmed to emit a certain wavelength, such as the 222 nm wavelength discussed above.

Configurations herein are based, in part, on the observation that personal devices such as cellphones, smartphones and tablets often employ a utility lighting accessory operable as a flashlight. Since most adults carry some form of personal device, the utility light feature is readily accessible. It may be further observed that common touch surfaces, for example public seats and benches, sanitary facilities and mass transit, frequently undergo successive touching/physical contact. It would be beneficial to combine the widespread portability of personal devices with an illumination source adapted to irradiate and eliminate surface pathogens. Accordingly, configurations herein substantially overcome the shortcomings of conventional periodic cleaning by integrating an anti-pathogenic illumination source with a personal device for portable and available access to a surface sterilization means for everyday usage.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

In a particular configuration, the personal antimicrobial light device is based on a host device having a battery, processor and telecommunications hardware/software, and having control logic on the host device for performing various telecommunications and media operations, such as voice, text, video as well as a variety of applications "apps" for entertainment, interaction and information. A light source on the host device is responsive to the control logic for emitting an antimicrobial light and directing the antimicrobial light at a target surface for disinfection. An actuation function in the control logic is responsive to the user for actuating the light source. The actuation function integrates with the telecommunications hardware, such as a utility "flashlight" panel or via a separate app on the personal device for accessing and powering the light receptacle (LED). In general, the light source has a predetermined wavelength based on an antimicrobial effect of the wavelength. Far UVC (UV-C) light has little harmful side effects while having efficient antimicrobial properties.

Retrofitting into existing devices, or manufacture of new devices with the antimicrobial light are both viable methods of integrating an antimicrobial light into a personal electronic device. Installation includes identifying a utility light feature of a personal device, such that the personal device has telecommunications circuits and a graphical user interface (GUI). A typical personal device architecture is well suited to receiving the disclosed technology based on external LEDs and associated controls. The personal device is provided with a light emission source having a predetermined wavelength selected based on antimicrobial properties. The light emission source is responsive for activation by the utility light feature. This may involve replacing older, visible/illumination light LEDs with a UVC light, or at least programming the LED with the UVC wavelength, around 222 nm, or other suitable wavelength. The light emission source need only receive a signal from the GUI based on a user request for invoking the utility light feature, and irradiates a target region in the emission range of the light emission source for disinfecting the target region.

Figure 1:
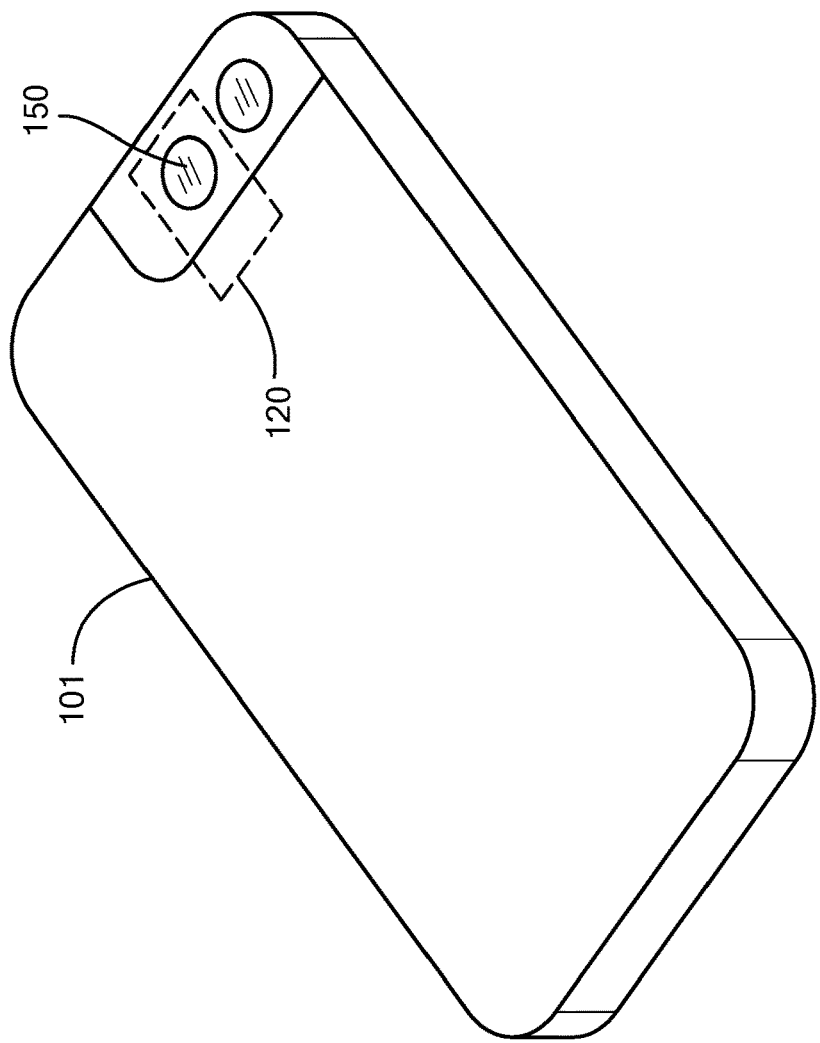
FIG. 1 is a context view of the antimicrobial light source in conjunction with a personal device.

FIG. 1 is a context view of the antimicrobial light source in conjunction with a personal device. The personal device 101 performs a method of disinfection via a smartphone flashlight for quantifying and precisely disinfecting surfaces with an antimicrobial light emitted from the smartphone flashlight. The antimicrobial light source 150, in one configuration, is defined by a light emitting diode (LED) providing an antimicrobial and safe light emission having a wavelength around 222 nm or 405 nm. The antimicrobial light source is integrated into the personal device 101, which may be any suitable electronic device adapted for emitting light such as a tablet, iPad, smartwatch or laptop. Personal devices for telecommunications, Internet browsing, and other related personal computing and communication tasks take a myriad of forms, but generally fall into several categories of devices colloquially known as a cellphone, smartphone, wireless phone, mobile device and simply "phone."

In the configurations herein, the antimicrobial light source may be implemented in several forms. The antimicrobial light source 150 (light source) may be integrated in the personal device 101 in lieu of the native utility light, in addition to the utility light, or as a retrofit apparatus adapted for attachment onto a smartphone or electronic apparatus to enable antimicrobial light disinfection. Associated power and switching circuitry 150 receives the light source, typically an LED bulb, in the device case 110.

Figure 2:
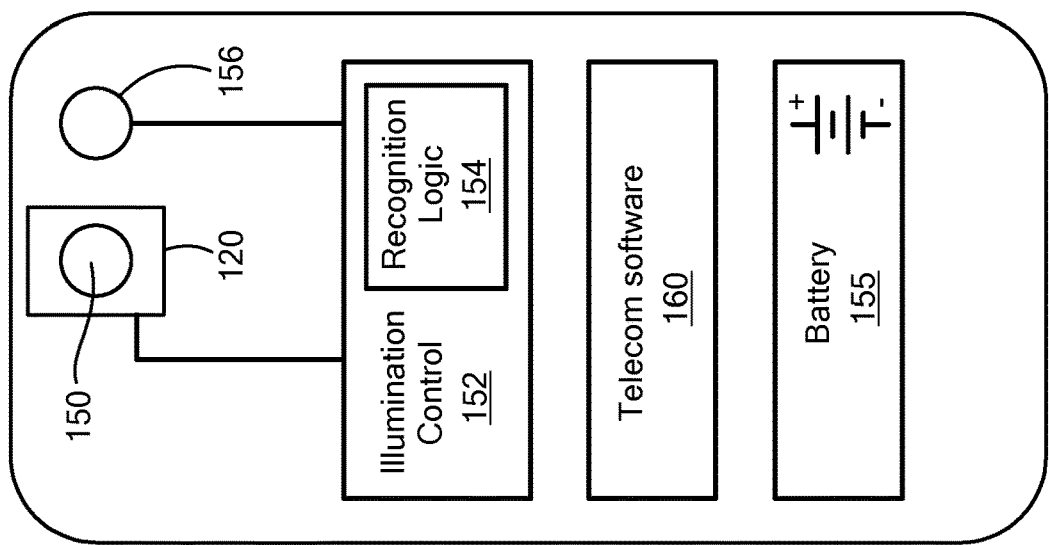
FIG. 2 is a schematic diagram of a personal device integrated with the antimicrobial light source.

FIG. 2 is a schematic diagram of a personal device integrated with the antimicrobial light source 150. The personal device 101 is augmented with illumination control 152 and the light source 150 provides an antimicrobial smartphone flashlight system with portability for everyday usage to irradiate various surfaces encountered by the user. The illumination control 152 may also quantify and precisely disinfect surfaces by determining a distance and surface quality of the disinfection target. Power is provided by the native smartphone battery 155, as LEDs typically have a low current draw, commensurate with the load already presented by a conventional smartphone utility light feature.

In a particular configuration, the illumination control 152 includes object recognition logic 154 for determining the distance and surface quality of a target object or surface. A visual recognition sensor 156 such as a camera or charge coupled device (CCD) conveys optical properties 156' of a target surface. Current cleanliness of the surface may also be determined from the optical sensor for use in evaluating an irradiation time. The illumination logic energizes the antimicrobial light source 150 embedded in the smartphone flashlight as the personal device 101 is disposed the around a target object to be disinfected. The illumination control 152 invokes a set of instructions in the object recognition logic for performing a 3D scan of the target object, and calculates a surface distance and surface quality or properties and a required antimicrobial light exposure time needed for a specified level of disinfection.

The illumination control 152 may be in the form or an application (app), integrated in the native telecommunications circuitry and software 160 of the personal device 101, or otherwise integrated via the memory, control logic and processor inherent in the personal device 101. In this manner, the illumination control 152 is invoked via an actuation function in the control logic and responsive to the user for actuating the light source 150, where the actuation function is integrated with the native telecommunications hardware.

In this manner, surface disinfection by a user invokes a host device having a battery 155 and telecommunications hardware 160, and activates the light source 150 on the host device responsive to the control logic for emitting an antimicrobial light and directing the antimicrobial light at a target surface or object for disinfection.

Figure 3:
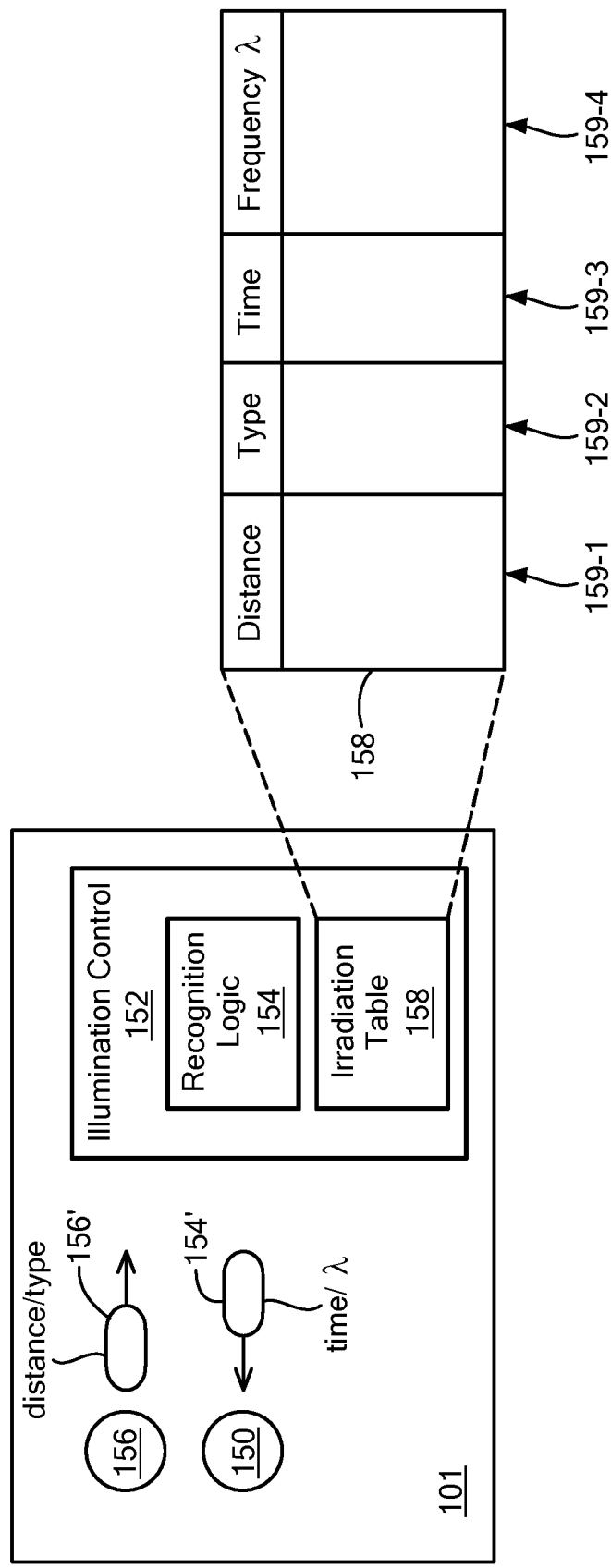
FIG. 3 is a block diagram of the personal device of FIGS. 1 and 2 and illumination logic.

FIG. 3 is a block diagram of the personal device of FIGS. 1 and 2 and illumination logic. In a particular configuration, a user employs the personal device 101 configured as a smartphone flashlight with the light source 150 moved around a target object for bathing surfaces in antimicrobial light. The object recognition logic 154 renders, on a smartphone display, surface cleanliness values, discussed further below in FIG. 4. Since most devices have a utility lighting feature, the antimicrobial light source 150 may be an additional LED with specific wavelength or LED with capability of emitting various wavelengths, where the illumination control 152 radiates the appropriate light wavelength for utility lighting or sterilizing irradiation. The personal device 101 includes, at a minimum, a means for turning an antimicrobial flashlight on, a means for disposing the flashlight around a target object to be disinfected, and a means for invoking smartphone software for performing a 3D scan of the target object, calculating a surface distance and a required antimicrobial light exposure time needed for specified level of disinfection.

The object recognition logic 154 defines a range detection circuit configured for identifying a distance to the target surface, and disinfectant logic for determining, based on a luminescence of the emitted light and the distance to the target surface, a duration of light emittance for disinfecting the target surface. The disinfectant logic may include an irradiation table 158 accessible by the object recognition logic 154. The irradiation table 158 includes entries for a time 159-3 and wavelength 159-4 of irradiation based on a mapping of distance 159-1 and surface type 159-2. The disinfectant logic is configured to compute the duration and wavelength based on a type of the object detected by the object recognition circuit by mapping the distance and surface type 156' received via the optical sensor 156, which may be the native camera. Depending on the illumination source 150, the wavelength may be a constant and only the time of irradiation varied. As a safety measure, the object recognition logic (circuit) 154 may identify vulnerable entities such as small children and pets to whom the UV irradiation may be harmful. The disinfectant logic is responsive to detection of a vulnerable target for deactivating the light source based 150 on the presence of the vulnerable target.

In general, the range detection circuit is configured for identifying a distance to the target surface. Disinfectant logic, such as from an app, is launchable to determine, based on a luminescence of the emitted light and the distance to the target surface, a duration of light emittance for disinfecting the target surface. Different surfaces, such as metal doorknobs, vinyl seats, wooden benches, may all provide differing longevity to contaminants. Also, different LEDs emit the far UVC light at different intensities (i.e. brightness). An object recognition circuit may invoke a device camera to compute the duration based on a type of the object detected by the object recognition circuit, to ensure a sufficient radiation of the target surface. The illumination control 152 directs the light source 150 to activate according to the computed time and wavelength 154'.

The object recognition circuit may also reduce the intensity of the light source or terminate altogether if a sensitive or vulnerable target object is illuminated. For example, recognition of a small child or infant for which exposure may be harmful can be detected and exposure avoided. The disinfectant logic is therefore responsive to detection of a vulnerable target for deactivating the light source based on the presence of the vulnerable target. Other safety features, my be incorporated to prevent unintended irradiation of light sensitive targets, such as recent skin injuries, light sensitive materials, close optical contact (child lifting light adjacent eyes, etc.). and others may be recognized and acted upon.

Figure 4:
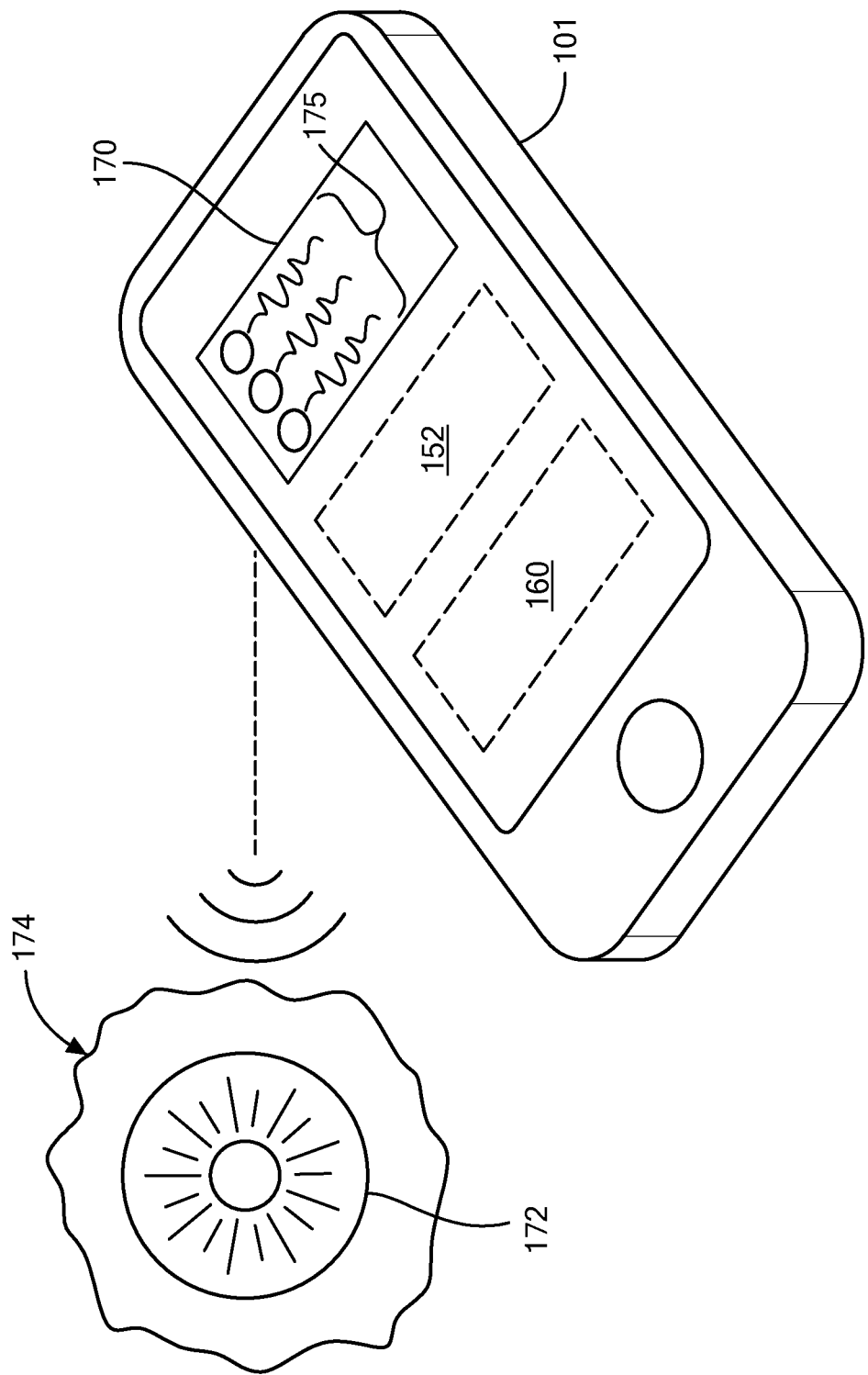
FIG. 4 is a remote activation configuration of an external antimicrobial light source.

FIG. 4 is a remote activation configuration of an external antimicrobial light source. FIG. 4 depicts app based usage including a graphical user interface (GUI) 170 having a utility lighting selection 175, such that the antimicrobial light wavelength is emitted responsive to the GUI 170. In addition to control of a light source 150 integrated with the personal device 101, the antimicrobial light may take the form of an attachable or adherable fixture 172 for semi-permanent attachment adjacent the target area. The antimicrobial light mat be attached for directing the emitted light towards a high contact area, for example doorknobs or common area seating. A remote personal device may be invoked for controlling the emitted light, similar to control of the on-board LED discussed above. The fixture 172 employs an affixation region 174, such as an adhesive, tether or strap, configured for attachment in an area for decontamination. The fixture 172 is responsive to a control device for emitting the antimicrobial light, i.e. from a remote smartphone. Placement of the fixture above or adjacent to high touch areas allows decontamination on demand via the app.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. An antimicrobial smartphone flashlight, further comprising:
   a light source adapted to irradiate a target surface with emitted light having antimicrobial properties;
   a range detection circuit, the range detection circuit configured for identifying a distance to the target surface; and
   disinfectant logic, the disinfectant logic for determining, based on a luminescence of the emitted light, a type of the target surface and the distance to the target surface, a duration of light emittance for disinfecting the target surface.

2. The device of claim 1 comprising an integrated antimicrobial light source, the light source powered by a smartphone battery.

3. The device of claim 2 wherein the antimicrobial light source further comprises:
   a light emitting diode (LED), the LED providing an antimicrobial and safe light emission having wavelengths including at least one of far UVC or antimicrobial visible blue light.

4. The antimicrobial light source of claim 3, wherein:
   the antimicrobial light source further comprises an additional LED with specific wavelength or LED with capability of emitting various wavelengths.

5. The antimicrobial light source of claim 3 wherein the antimicrobial light source is integrated into a smartphone.

6. The antimicrobial light source of claim 5 further comprising:
   a retrofit apparatus adapted for attachment onto the smartphone to enable antimicrobial light disinfection.

7. An antimicrobial smartphone flashlight system, further comprising:
   means for invoking smartphone software for performing a 3D scan of a target object, and based on the 3D scan, calculating surface distance, area, shape, and a required antimicrobial light exposure time needed for specified level of disinfection;
   means for turning an antimicrobial flashlight on for a duration based on the exposure time; and
   means for disposing the flashlight around a target object to be disinfected.

8. The system of claim 7 comprising a system of quantifying and precisely disinfecting surfaces with an antimicrobial smartphone flashlight.

9. An integrated antimicrobial light device, further comprising:
   an antimicrobial light source for emitting light having antimicrobial properties;
   a range detection circuit, the range detection circuit configured for identifying a distance to a target surface; and
   disinfectant logic, the disinfectant logic for determining, based on a luminescence of the emitted light and the distance to the target surface, a duration of light emittance for disinfecting the target surface.

10. The device of claim 9 comprising an electronic device including one of a tablet, iPad, smartwatch, smartphone, 3D scanner, computer, laptop, camera, sensor, robot, instrument, or light emitter.

11. The device of claim 9 wherein the device quantifies and precisely disinfects surfaces with safe, antimicrobial light.

12. The antimicrobial light source of claim 9 wherein the antimicrobial light source is integrated into an electronic device.

13. The antimicrobial light source of claim 9 further comprising:
   a retrofit apparatus adapted for attachment onto an electronic apparatus to enable antimicrobial light disinfection.

14. The light of claim 9 comprising safe, antimicrobial wavelengths including at least one of far UVC or antimicrobial blue light.

15. The device of claim 9 further comprising a user interface (UI) having a utility lighting selection, a wavelength of the antimicrobial light wavelength emitted selectable via the UI.

16. The device of claim 9 further comprising an object recognition circuit, the disinfectant logic configured to compute the duration based on a type of the object detected by the object recognition circuit.

17. The device of claim 9 further comprising an object recognition circuit, the disinfectant logic responsive to detection of a vulnerable target and deactivating the light source based on the presence of the vulnerable target.

18. The device of claim 17 further comprising:
   a translucent material in optical communication with the light source, the translucent material formed around a region for disinfectant.

19. The device of claim 9 further comprising:
   an affixation region, the affixation region configured for attachment in an area for decontamination, wherein device hardware is responsive to a control device for emitting the antimicrobial light.

\* \* \* \* \*